US012653720B2

(12) United States Patent
Wojciechowski et al.

(10) Patent No.: US 12,653,720 B2
(45) Date of Patent: Jun. 16, 2026

(54) CONTROLLED OXYGEN DRESSING

(71) Applicant: Advanced Dressings, LLC, Cleveland, OH (US)

(72) Inventors: Timothy Wojciechowski, Westlake, OH (US); Thomas E. Lash, Chardon, OH (US); John Buan, Maple Grove, MN (US); Richard L. Middaugh, Rocky River, OH (US); Edward Armstrong, Chagrin Falls, OH (US)

(73) Assignee: AATRU MEDICAL, LLC, Cleveland, OH (US)

( * ) Notice: Subject to any disclaimer, the term of this patent is extended or adjusted under 35 U.S.C. 154(b) by 425 days.

(21) Appl. No.: 18/008,704

(22) PCT Filed: Jun. 15, 2021

(86) PCT No.: PCT/US2021/037333
§ 371 (c)(1),
(2) Date: Dec. 8, 2022

(87) PCT Pub. No.: WO2021/257508
PCT Pub. Date: Dec. 23, 2021

(65) Prior Publication Data
US 2023/0210701 A1 Jul. 6, 2023

Related U.S. Application Data

(60) Provisional application No. 63/039,664, filed on Jun. 16, 2020.

(51) Int. Cl.
A61F 13/0203 (2024.01)
A61F 13/00 (2024.01)
A61F 13/0246 (2024.01)

(52) U.S. Cl.
CPC .......... *A61F 13/022* (2013.01); *A61F 13/025* (2013.01); *A61F 2013/00872* (2013.01); *A61F 2013/00902* (2013.01)

(58) Field of Classification Search
CPC ................ A61F 13/00; A61F 13/00021; A61F 13/00046; A61F 13/022; A61F 13/025; (Continued)

(56) References Cited

U.S. PATENT DOCUMENTS

| | | | | |
|---|---|---|---|---|
| 10,046,095 B1 * | 8/2018 | Middaugh | ............. | A61M 1/962 |
| 10,449,094 B2 | 10/2019 | Donda | | |
| 2015/0283287 A1 * | 10/2015 | Agarwal | ................ | A61L 15/26 424/650 |

FOREIGN PATENT DOCUMENTS

| | | |
|---|---|---|
| WO | 2020046907 | 3/2020 |
| WO | 2020046935 | 3/2020 |

OTHER PUBLICATIONS

International Search Report filed in PCT/US2021/037333 mailed Oct. 1, 2021.

* cited by examiner

*Primary Examiner* — Caitlin A Carreiro
(74) *Attorney, Agent, or Firm* — Rankin, Hill & Clark LLP

(57) ABSTRACT

A controlled oxygen dressing includes a flexible drape that is selectively permeable to air and is adhere to skin to define a first volume around a tissue site. A cover layer, impermeable to air, is sealed to the drape to thereby define a second volume between the cover layer the drape. An oxygen scavenger is arranged in the second volume and consumes oxygen in the second volume, which produces an oxygen concentration differential between the first and second volumes, This differential causes oxygen to diffuse through a covered portion of the drape, from the first volume to the (Continued)

second volume, thus decreasing the amount of oxygen in the first volume. Oxygen entering into the first volume from the surrounding environment diffuses through a non-covered portion of the drape. Therefore, an area of the cover layer can be selected to produce a desired level of oxygen in the first volume.

14 Claims, 2 Drawing Sheets

(58) Field of Classification Search
CPC ................ A61F 13/02; A61F 13/01046; A61F 13/0289; A61F 2013/00872; A61F 2013/00902
USPC ................................................ 602/41, 54, 58
See application file for complete search history.

CONTROLLED OXYGEN DRESSING

BACKGROUND

Effective tissue treatment may include creating an environment around a tissue site that has a controlled level of oxygen.

SUMMARY

A controlled oxygen dressing for tissue treatment includes a drape permeable to air, having a first area, including a skin-facing surface and an exposed surface which is opposite the skin-facing surface. The drape is configured to be adhered to skin and thereby define a first volume between the skin-facing surface and the skin. The system also includes a cover layer configured to be sealed to the exposed surface and thereby cover a covered portion of the exposed surface of the drape and define a second volume between the cover layer and the covered portion. The system also includes an oxygen scavenger configured to be arranged in the second volume so as to remove oxygen from the second volume and thereby provide a desired level of oxygen in a first volume.

A temperature-independent method of controlling oxygen around a tissue site includes arranging a flexible drape over the tissue site to thereby define a first volume between the drape and the tissue site. The drape includes a skin-facing surface facing the tissue site and an exposed surface facing away from the tissue site. The drape is permeable to air. The method also includes determining, based on a desired oxygen level for the first volume, a portion of the exposed surface of the drape that is to have restricted exposure to a surrounding atmosphere. The method also includes covering the portion with a cover layer of equal area, thereby defining a covered portion of the exposed surface of the drape and a second volume between the cover layer and the covered portion. The cover layer restricts ingress of air from the surrounding atmosphere, through the covered portion, and into the first volume. The method also includes arranging an oxygen scavenger in the second volume to thereby remove oxygen from the second volume, which produces an oxygen level in the first volume lower than in the surrounding atmosphere.

A method of manufacturing a dressing system, includes preparing a flexible drape permeable to air, having a first area, including a skin-facing surface and an exposed surface opposite to the skin-facing surface, and an adhesive gasket on the skin-facing surface configured to adhere the drape to skin and thereby define a first volume between the skin-facing surface and the skin. The method also includes preparing a cover layer including a bottom surface and a seal on the bottom surface configured to seal the cover layer to the exposed surface and thereby cover a covered portion of the exposed surface of the drape and define a second volume between the cover layer and the covered portion. The method also includes arranging an oxygen scavenger on the exposed surface of the drape or on the bottom surface of the cover layer such that when the cover layer is sealed to the exposed surface, the oxygen scavenger is arranged in the second volume to thereby remove oxygen from the second volume and provide a desired level of oxygen in the first volume.

DETAILED DESCRIPTION

Figure 1:
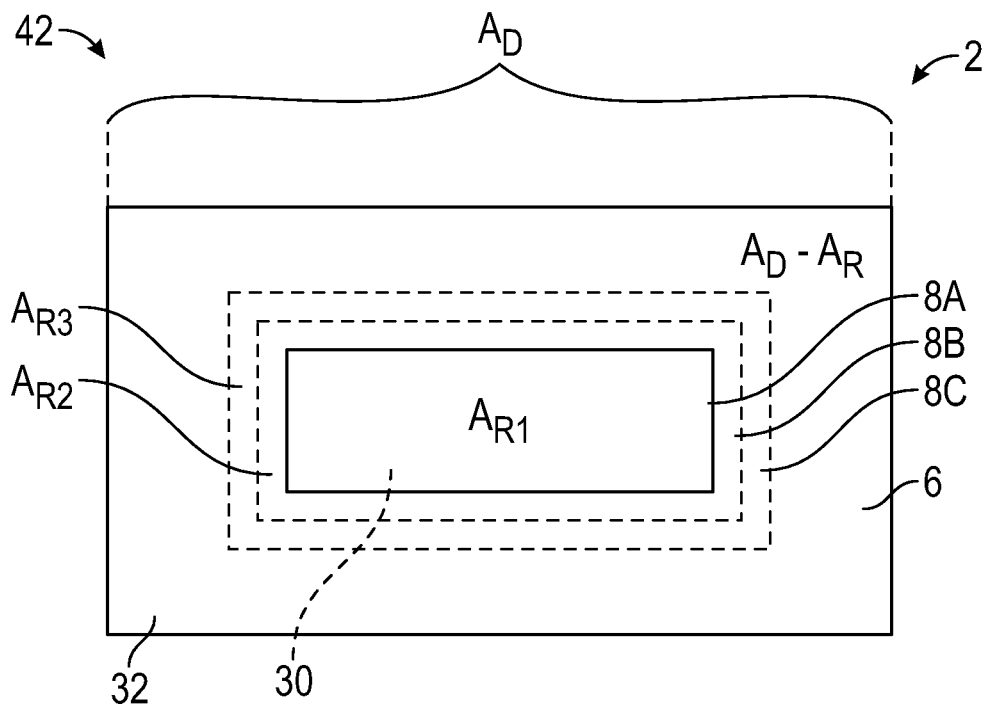
FIG. 1 is a plan view of a controlled oxygen dressing system according to the present subject matter.

A tissue treatment device, in the form of a controlled oxygen dressing, provides a controlled oxygen environment around a tissue site. The environment is a local environment created by the dressing around the tissue site. The environment has a level of oxygen ($O_2$) gas that is less than that contained on average in the atmosphere, which includes about 20.95% oxygen gas. However, the environment around a tissue site may still be at normal atmospheric pressure. In other words, unlike some negative pressure wound therapy dressings that employ an oxygen scavenger to remove oxygen from beneath a drape to provide therapeutic negative pressure to a tissue site, which therapeutic negative pressure is typically between −60 and −125 mmHg with respect to atmospheric pressure, the subject dressing does not lower the pressure around a tissue site to a therapeutic negative pressure. As described herein, the level of oxygen in the local environment created by the dressing may be controlled by adjusting the configuration (e.g. area or relative areas) of various components of the dressing.

In general, and referring to the figures, a controlled oxygen dressing 2 includes a continuous drape 6 that is selectively permeable to air and is configured to be adhered to skin 12 around a tissue site 4 to define a first volume 14 around the tissue site 4. A cover layer 8, which is impermeable to air, is sealed to an exposed surface 18 of the drape 6, to thereby define a covered portion 30 of the drape 6, and a second volume 22 between the cover layer 8 and the covered portion 30. An oxygen scavenger 10 is arranged in the second volume 22 and consumes/scavenges oxygen in the second volume 22. Because of this, an oxygen concentration differential is established on either side of the covered portion 30 of the drape 6, and between the first volume 14 and the second volume 22; where the second volume 22 has less oxygen than the first volume 14. This differential causes oxygen to diffuse from the first volume 14, through the covered portion 30, and into to the second volume 22, thus decreasing the amount of oxygen in the first volume 14. However, the cover layer 8 covers the covered portion 30 of the drape 6, and being impermeable to air, thus restricts ingress of air from the surrounding environment, through the covered portion 30, and into the first volume 14, and thus limits oxygen diffusion from the surrounding environment 34 into the first volume 14 so that it occurs only through the area of the non-covered portion 32 of the drape 6. Therefore, the area of the cover layer 8 determines the area of the non-covered portion 32, i.e. the area available for diffusion of oxygen from the surrounding environment 34 into the first volume 14; and also the area of the covered portion 30, i.e. the area available for diffusion of oxygen from the first volume 14 into the second volume 22. As such, the area of the cover layer 8 determines the rate of oxygen diffusion from the surrounding environment 34 to the first volume 14, and from the first volume 14 to the second volume 22. As such, an area of the cover layer 8 can be selected to produce a desired level of oxygen in the first volume 14.

More specifically, the controlled oxygen dressing 2 is provided for treating a tissue site 4 to which it is applied. The tissue site 4 may include, but is not limited to, a wound, an incision, or skin 12 where there is no wound or incision. The dressing 2 treats the tissue site 4 by providing a controlled oxygen environment around the tissue site 4. The controlled oxygen environment has reduced oxygen levels, i.e. below 20.95%. The dressing 2 includes a drape 6, a cover layer 8, and an oxygen scavenger 10 arranged between the drape 6 and cover layer 8. The level of oxygen in the environment created around the tissue site 4 is controlled by adjusting a ratio of an area of the drape 6 to an area of the cover layer 8.

The drape 6 includes a skin-facing surface 16, an opposite exposed surface 18, and a thickness ($T_1$). The drape 6 may be a thin flexible continuous sheet, such as a flexible elastomeric film. By "continuous", it is meant that the drape 6 does not include voids, apertures, pores, holes, or other openings that extend from the skin-facing surface 16 to the exposed surface 18, and that allow bulk transfer or a continuum flow of air through its thickness ($T_1$). However, the continuous drape 6 may have properties that allow diffusion/permeation of air, rather than bulk transfer or continuum flow of air, through its thickness ($T_1$), where air on one side of the drape 6 adsorbs into the drape 6, diffuses through the thickness ($T_1$) of the drape 6, and then desorbs out of the other side of the drape 6, which is also referred to as permeation through the drape 6. In this respect, the drape 6 is selectively permeable to air, e.g. to gases in air (oxygen, nitrogen, carbon dioxide, etc.) and optionally also to water vapor in air. The drape 6 may be impermeable to water, but may be permeable to water vapor. The drape 6 may have a transmission rate through its thickness ($T_1$) normalized to 1 mil, at standard temperature and pressure (STP) and 0% relative humidity (RH), of greater than 30 $cm^3/m^2/24$ hr for oxygen gas (i.e. oxygen transmission rate, or oxygen permeability). The drape 6 may also have a transmission rate through its thickness ($T_1$) normalized to 1 mil, at STP and 0% RH, of less than 10 $g/m^2/24$ hr for water vapor. The drape 6 may also have one or more independent transmission rates through its thickness ($T_1$) normalized to 1 mil, at STP and 0% RH, of greater than 90 $cm^3/m^2/24$ hr for carbon dioxide gas, greater than 6 $cm^3/m^2/24$ hr for nitrogen gas, less than 10 $g/m^2/24$ hr for water vapor, and less than 1 $g/m^2/24$ hr for liquid water.

The thickness ($T_1$), composition, or configuration of the drape 6 may be adjusted so that the drape 6 has a desired air/oxygen transmission rate through its thickness ($T_1$). The drape 6 may have an area (first area) as determined by the area ($A_D$) of the exposed surface 18.

The drape 6 may include polymer materials including, for example, polyurethane, polyethylene, polypropylene, polyether, polyamide, etc., or combinations or copolymers thereof. For example, the thin film material from which the drape 6 is made may be constructed of polyurethane or other semi-permeable material such as that sold under the Tegaderm® brand or 9834 TPU tape available from 3M. Similar films available from other manufacturers may also be used.

Figure 2:
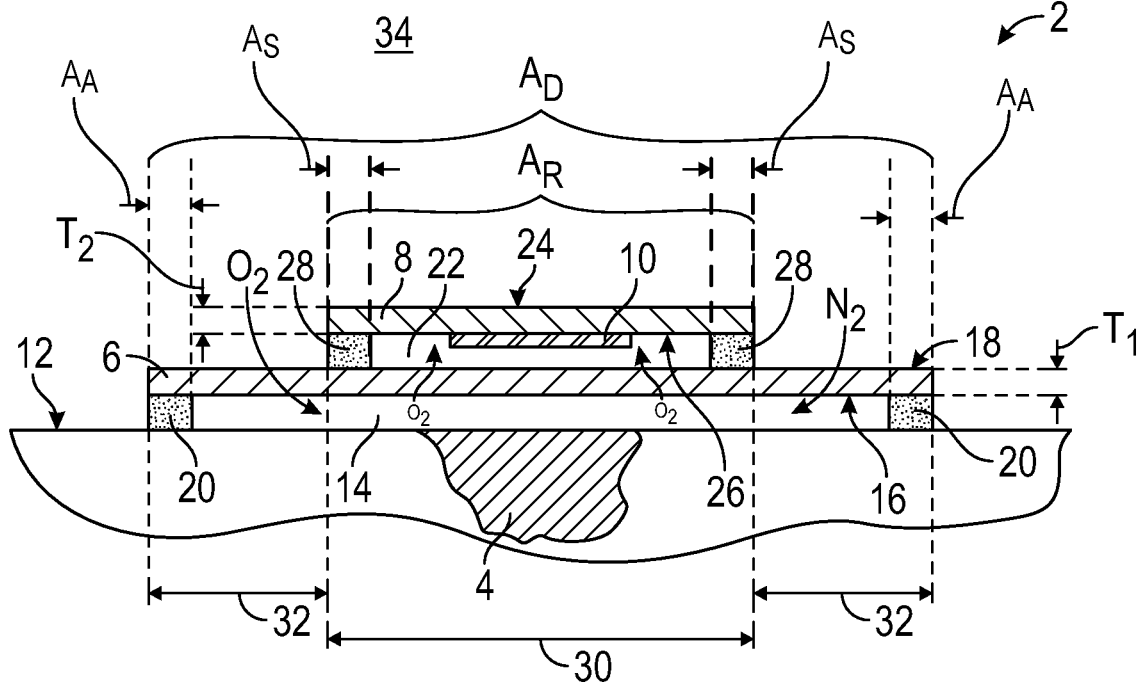
FIG. 2 is a schematic cross-sectional side view of a controlled oxygen dressing applied to skin according to the present subject matter.

The drape 6 may include an adhesive gasket 20 for adhering the drape 6 to the skin 12. The adhesive gasket 20 may be arranged on the skin-facing surface 16 and around a periphery of the drape 6 (FIG. 3) to form a perimeter that completely surrounds the tissue site 4 (FIG. 2). The adhesive gasket 20 may occupy a certain portion of the skin-facing surface 16 of the drape 6 as determined by the area ($A_A$) of the adhesive gasket 20. The adhesive gasket 20 may include a gasket material containing silicone, rubber, polymer, metal, foam, and acrylic-based adhesives, other adhesives, or other types of materials and adhesives. The adhesive gasket 20 may include a pressure sensitive adhesive, and may include a resealable adhesive to allow for removal and later reattachment of the drape 6 to the skin 12, which can allow for inspection of the tissue site 4. The adhesive gasket 20 may have the same or lower permeability as the drape 6. The adhesive gasket 20 may be a compliant material having a certain cross-sectional height (which may be measured with respect to FIG. 2 from the skin 12 to the skin-facing surface 16 of the drape 6) so as to accommodate and account for undulations in the underlying skin 12, yet still being able form an air-tight seal with the skin 12.

When the drape 6 is adhered to the skin 12 around the tissue site 4, the drape 6, the adhesive gasket 20, and the portion of the skin 12 under the drape 6 and within the perimeter of the adhesive gasket 20 collectively define the boundaries of a first volume 14 around the tissue site 4. This first volume 14 functions as the controlled oxygen environment around the tissue site 4.

The cover layer 8 is adhered to the exposed surface 18 of the drape 6 to thereby define a second volume 22 above the first volume 14, and arranged on either side of the drape 6. The second volume houses the oxygen scavenger 10. The cover layer 8 includes a top surface 24, an opposite bottom surface 26, and a thickness ($T_2$). When the cover layer 8 is adhered to the drape 6, the bottom surface 26 faces the exposed surface 18 of the drape 6, and the top surface 24 faces away from the drape 6.

The cover layer 8 may include a thin flexible continuous layer, such as including a flexible elastomeric film. Being continuous, the cover layer 8 is thus free of voids, apertures, pores, holes, or other openings that extend from the bottom surface 26 to the top surface 24 through the thickness ($T_2$) of the cover layer 8, and thereby prevents bulk transfer or continuum flow of air or water through its thickness ($T_2$). Moreover, the cover layer 8 may be resistant to permeation through its thickness ($T_2$) of gases and water vapor in air, and to water. The cover layer 8 may inhibit the ingress (e.g. diffusion) of air and water through its thickness ($T_2$), by having individual transmission rates (i.e. permeability) through its thickness ($T_2$) that are equal to or less than the drape. The transmission rate may be normalized to 1 mil, at STP and 0% RH, of less than 30 $cm^3/m^2/24$ hr for oxygen gas. The cover layer 8 may also have one or more independent transmission rates through its thickness ($T_2$) normalized to 1 mil, at STP and 0% RH, of less than 90 $cm^3/m^2/24$ hr for carbon dioxide gas, less than 6 $cm^3/m^2/24$ hr for nitrogen gas, less than 10 $g/m^2/24$ hr for water vapor, and less than 1 $g/m^2/24$ hr for liquid water.

The cover layer 8 may include a base polymer film coated or filled with a material that decrease the transmission rate of air and water through its thickness ($T_2$), and these coating or filling materials may include blocking materials of metal, graphene, polyvinylidene chloride, polyvinyl alcohol, ethylene vinyl alcohol, or combinations thereof. The base polymer film to be coated or filled with these blocking materials may include high density polyethylene, polyethylene terephthalate, polylactic acid, polypropylene, polystyrene, etc., or combinations thereof. The cover layer may also include additional layers to form a multilayer structure including additional layers, which may include these blocking materials. The cover layer 8 may be metallized to prevent the ingress of air into the second volume 22 or into the first volume 14. In order to prevent the ingress of air, the cover layer 8 may be a metalized polymer film including a metal layer arranged on a polymer film (e.g. polyester, polyethylene, polypropylene, polylactic acid, polyimide, fluoropolymer, polyether ether ketone, polyvinylidene chloride, polystyrene, polyethylene terephthalate, ethylene vinyl alcohol, nylon, polyethylene terephthalate). The metal may be a foil or coating layer, and may have a thickness of, for example, from 10 nm to 10 μm. The metal layer may include various metals, for example aluminum, nickel, copper, or chromium. The metal layer may be laminated with or coated on the polymer film. Coating of the metal layer on the polymer film may be accomplished by various deposition techniques, such as physical vapor deposition including a variety of vacuum deposition methods. The metalized polymer film may include further layers, such as a protection layer over the metal layer.

The thickness ($T_2$) of the cover layer 8, e.g. a thickness of the base polymer film and/or a thickness of the coating material, type of material used, and number of layers of the cover layer 8 may be adjusted so that the cover layer 8 has a sufficiently low air/water transmission rate. The transmission rate of air through the thickness ($T_2$) of the cover layer 8 may be the same, or less than the transmission rate of air through the thickness ($T_1$) of the drape 6. In other words, the permeability of air through the cover layer 8 may be the same or less than the permeability of air through the drape 6.

The cover layer 8 may include a seal 28 for adhering the cover layer 8 to the exposed surface 18 of the drape 6. The seal 28 may be arranged on the bottom surface 26 and around a periphery of the cover layer 8 (FIG. 3) to form a perimeter that completely surrounds oxygen scavenger 10 (FIG. 2) when the cover layer 8 is sealed to the drape 6. The seal 28 may occupy a certain portion of the bottom surface 26 of the drape 6 as determined by the area ($A_S$) of the seal 28. The seal 28 may include an adhesive gasket, adhesives, hydrogel material, silicone material (e.g. silicone gel), or any other material that can inhibit the migration of air and liquid from the surrounding environment 34 into the second volume 22. Using an adhesive gasket as the seal 28 may allow the cover layer 8 to accommodate undulations in the underlying exposed surface 18 of the drape 6 (such as if the drape 6 is contoured to adhere to the underlying skin 12), yet still form an air-tight seal with the drape 6. The seal 28 may have the same or lower permeability to air and water as the cover layer 8. The seal 28 may be resealable to allow for sealing the cover layer 8 to the drape 6, and then also for later removal of the cover layer 8 from the drape 6 to place or replace the oxygen scavenger 10 in the second volume 22, and then resealing the cover layer over the oxygen scavenger 10.

When the cover layer 8 is adhered to the exposed surface 18 of the drape 6, the cover layer 8, the seal 28, and the covered portion 30 of the exposed surface 18 under the cover layer 8 and within the perimeter of the seal 28, collectively define the boundaries of a second volume 22, which houses the oxygen scavenger 10.

The cover layer 8 may have an area (second area) as determined by the area ($A_R$) of the top surface 24. This area ($A_R$) of the cover layer 8 corresponds to the area of the covered portion 30 of the exposed surface 18 of the drape 6. The non-covered portion 32 of the drape 6, i.e. the portion of the exposed surface 18 that is not covered by the cover layer 8, is shown in FIG. 1 as ($A_D$–$A_R$). The area ($A_R$) of the cover layer 8 may be less than the area ($A_D$) of the drape 6.

As schematically shown in FIG. 2, since the drape 6 is selectively permeable to air, air (depicted as $O_2$ and $N_2$ gases) from the surrounding environment 34 (e.g. surrounding atmosphere or ambient) diffuses through the non-covered portion 32 of the drape 6 and into the first volume 14.

However, this diffusion of air/oxygen from the surrounding environment 34 and into the first volume 14 is limited by the area of the non-covered portion 32, and the transmission rate of air/oxygen through the thickness ($T_1$) of the drape 6. At the same time, the oxygen scavenger 10 consumes oxygen in the second volume 22, which creates an oxygen concentration imbalance on either side of the covered portion 30 of the drape 6 (i.e. between the first volume 14 and the second volume 22. Because of this imbalance, oxygen is urged to enter into the second volume 22. However, because the cover layer 8 is impermeable to air, including oxygen gas, the only source of oxygen to enter into the second volume 22 is from the first volume 14 through the covered portion 30 of the drape 6; while the only source of oxygen to enter into the first volume 14 is from the surrounding environment 34 through the non-covered portion 32 of the drape 6, thus the cover layer 8 limits (e.g. eliminates) the ingress of air through the covered portion 30 into the first volume 14. As such, oxygen in the first volume 14 is urged by this oxygen concentration imbalance to diffuse out of the first volume 14, through the covered portion 30, and into the second volume 22. The amount of oxygen diffusing into the first volume 14 from the surrounding environment 34 is limited by the transmission rate for oxygen through the drape 6, and by the area ($A_D$–$A_R$) of the non-covered portion 32. If the area of the covered portion 30 is greater than the area of the non-covered portion 32, or if there is a greater oxygen concentration difference between the first and second volumes 14, 22 than between the surrounding environment 34 and the first volume 14, then more oxygen may diffuse out of the first volume 14 and into the second volume 22 than the amount that diffuses from the surrounding environment 34 and into the first volume 14. This limitation to the diffusion of oxygen into the first volume 14, coupled with the diffusion of oxygen out of the first volume 14 and into the second volume 22, thus may produce a reduced oxygen level in the first volume 14 that is less than 20.95%.

Although oxygen is removed from the first volume 14 and thus has a reduced amount of oxygen compared to the surrounding environment, the first volume 14 may maintain about the same pressure (e.g. atmospheric pressure) as the surrounding environment 34. This may occur because the drape 6 is flexible and thus may change shape as oxygen is transmitted through the drape 6 to the second volume 22 to be consumed by the oxygen scavenger 10. The drape 6 may thus controllably collapse toward to the tissue site 4 as oxygen is transmitted out of the first volume 14 and into the second volume 22, and thus allows for a decrease in size of the first volume 14 as this occurs. However, because the size of the first volume 14 is reduced, the first volume 14 may maintain atmospheric pressure, or a pressure close to atmospheric pressure. In this process, other gases (i.e. $N_2$ and $CO_2$) may not be removed from the first volume 14 by the oxygen scavenger 10. As the oxygen scavenger 10 consumes oxygen in the second volume 22, oxygen is transmitted through the drape 6 from the first volume 14 to the second volume 22. This may produce a certain amount of negative pressure in the first volume 14. However, this negative pressure is only temporary, because it causes the flexible drape 6 to collapse such that the first volume 14 becomes smaller, thus greatly reducing or eliminating the negative pressure in the first volume 14 and bringing the pressure in the first volume 14 back toward atmospheric pressure. Moreover, oxygen being removed from the first volume 14 and being transmitted to the second volume 22 is at least partially being replaced by the oxygen being transmitted from the surrounding environment 34 into the first volume 14, albeit possibly at a slower rate. Thus, the controlled collapsing of the drape 6 toward the tissue site 4 as oxygen is consumed, may allow the first volume 14 to have a reduce oxygen level while being at or near atmospheric pressure. The drape 6 may inevitably offer a little resistance to collapsing, and that resistance, however low though it may be, might not be zero, and thus the pressure in the first volume 14 may inevitably be somewhat less than atmospheric.

The collapsing of the drape 6 toward the tissue site 4 may be possible by the dressing 2 including a compressible element arranged in the first volume 14, and which initially holds up the drape 6 away from the tissue site 4 a certain distance, but which compresses upon a reduction in pressure in the first volume, thus allowing the drape 6 to collapse and the first volume 14 to experience a reduction in volume and thus no or very little decrease in pressure. The compressible element may include an absorber material for absorbing exudate from the tissue site. 4.

The area $(A_D-A_R)$ available for permeation of oxygen from the surrounding environment 34 to the first volume 14 is the non-covered portion 32 of the drape 6, and such permeation of oxygen though the non-covered portion 32 occurs when the partial pressure of oxygen $(P_{O2})$ in the surrounding environment 34 $(P_{O2,surrounding\ atmosphere})$ is greater than the partial pressure of oxygen in the first volume 14 $(P_{O2,first\ volume})$. The area $(A_R)$ available for permeation of oxygen from the first volume 14 to the second volume 22 is the covered portion 30 of the drape 6, and such permeation of oxygen though the covered portion 30 occurs when the partial pressure of oxygen in the first volume 14 $(P_{O2,first\ volume})$ is greater than the partial pressure of oxygen in the second volume 22 $(P_{O2,second\ volume})$, which is a function of the oxygen scavenger 10 consuming oxygen in the second volume 22.

As will be appreciated, the adhesive gasket 20 may have an area, as determined by the area $(A_A)$ it occupies on the skin-facing surface 16 of the drape 6. The portion of the skin-facing surface 16 covered by the adhesive gasket 20 may be impermeable to air, such that oxygen does not permeate from the environment 34, through the area $(A_A)$ of the drape 6, and into the first volume 14. For simplicity, discussion of this area $(A_A)$ has been omitted elsewhere herein. However, when discussing the permeability of air/oxygen from the environment 34, through the non-covered portion 32 of the drape 6, and into the first volume 14, it will be understood that the non-covered portion 32 means the area $(A_D)$ of the drape 6 minus the area $(A_A)$ of the adhesive gasket 20, minus the area $(A_R)$ of the covered portion 30.

Likewise, the seal 28 may have an area, as determined by the area $(A_S)$ it occupies on the exposed surface 18 of the drape 6. The portion of the exposed surface 18 covered by the seal 28 may be impermeable to air, such that oxygen does not permeate from first volume 14, through the area $(A_S)$ of the drape 6, and into the second volume 22. For simplicity, discussion of this area $(A_S)$ has been omitted elsewhere herein. However, when discussing the permeability of air/oxygen from the first volume 14, through the covered portion 30 of the drape 6, and into the second volume 22, it will be understood that the covered portion 30 means the area $(A_R)$ of the cover layer 8 minus the area $(A_S)$ of the seal 28.

The rate of permeation through the covered portion 30 or the non-covered portion 32 is equal to the permeability P of the drape 6, times the relevant area of the covered portion 30 or the non-covered portion 32, respectively, times the pressure differential of oxygen across the covered portion 30 or the non-covered portion 32, respectively.

The effusion rate of oxygen from the surrounding environment 34 into the first volume 14 may be determined by the following equation:

$$dn/dt = P(A_{non-covered\ portion})(P_{O2,surrounding\ environment} - P_{O2,first\ volume})$$

where dn/dt is the effusion rate, P is the permeability, A is the area, and $P_{O2}$ is the partial pressure of oxygen.

The effusion rate of oxygen from the first volume 14 to the second volume 22 may be determined by the following equation:

$$dn/dt = P(A_{covered\ portion})(P_{O2,first\ volume} - 0)$$

At equilibrium, both effusion rates (dn/dt) are equal, so the permeability parameter P drops out and $P_{O2,first\ volume} = P_{O2,surrounding\ atmosphere}(A_D-A_R)/(A_D-A_R+A_{covered\ portion})$. In other words, $(A_D-A_R)$ is the area of the non-covered portion 32, and $(A_D-A_R+A_{covered\ portion})$ is the total area of the drape 6, i.e. the non-covered portion 32 plus the covered portion 30. The partial pressure of oxygen in the first volume 14 may be a function of the ratio of the area of covered portion 30 to the area of the non-covered portion 32. If the adhesive gaskets 20, 28 are relatively impermeable to oxygen, then the area $(A_A)$ of the adhesive gasket 20 can be excluded in the determination of the effusion rate of oxygen into the first volume 14, and the area $(A_S)$ of the adhesive gasket 28 can be excluded in the determination of the effusion rate of oxygen from the first volume 14 to the second volume 22. Instead of the ratio of non-covered area to total drape area, the controlling area ratio is the area available for effusion from the atmosphere to the first volume 14 to the total area available for oxygen effusion to and from the first volume 14. In other words, $P_{O2,first\ volume} = P_{O2,surrounding\ atmosphere}(A_D-A_R-A_A)/(A_D-A_A-A_S)$, since the areas $(A_A\ and\ A_S)$ are no longer available for permeation in either direction.

The concentration level of oxygen in the first volume 14 is a function of a ratio of the area of the cover layer 8 to the area of the drape 6. The amount of oxygen in the first volume 14 may be controlled by adjusting the relative areas of the cover layer 8 and drape 6. In other words, the area $(A_R)$ of the cover layer 8 may be adjusted with respect to the area $(A_D)$ of the drape 6 in order to adjust the oxygen levels in the first volume 14.

For example and with reference to FIG. 1, as the area of the cover layer 8 increases from $A_{R1}$ to $A_{R2}$ to $A_{R3}$ while the area of the drape 6 is kept the same, the area of the covered portion 30 increases and the area of the non-covered portion 32 decreases. With a relatively smaller non-covered portion 32, less oxygen from the surrounding environment 34 enters into the first volume 14 through the smaller non-covered portion 32. With a relatively larger covered portion 30, more oxygen leaves the first volume 14, diffuses through the covered portion 30, and enters into the second volume 22. As such, as the area of the cover layer 8 increases from $A_{R1}$ to $A_{R2}$ to $A_{R3}$, the first volume 14 experiences a decrease in the amount of oxygen therein. A similar result may be had by decreasing the area of the drape 6 while maintaining the area of the cover layer 8, or by decreasing the area of the drape 6 and increasing the area of the cover layer 8.

The various areas $A_{R1}$, $A_{R2}$, $A_{R3}$ of the cover layer 8 may be provided by individual cover layers having these areas, such as cover layers 8A, 8B, 8C shown in FIG. 1 having respective areas a shown. Alternatively, a single cover layer 8A having an area $A_{R1}$ may be provided, along with picture-frame-shaped additional covering layers. These picture-frame-shaped covering layers which may be added around the cover layer 8A on the exposed surface 18 of the drape 6 in order to increase the effective area of the cover layer to be the area of $A_{R2}$ or $A_{R3}$. In another alternative, a single cover layer 8C having the area $A_{R3}$ may be provided, which can have tear-off or cut-off sections to selectively decrease the area of the cover layer to correspond to areas $A_{R1}$ or $A_{R2}$.

Transmission rate of gas through a membrane depends on the pressure, concentration, and temperature of the molecules or solutes on either side of the membrane, as well as the permeability of the membrane to each solute. Here however, the amount of oxygen in the first volume 14 may be independent of temperature, since the only temperature-sensitive variable is the permeability constant P for the drape 6, which is canceled out in the calculation of partial pressure of oxygen in the first volume 14 (i.e. $P_{O2,first\ volume}$). As such, the dressing 2 may provide a temperature-independent oxygen level around the tissue site 4.

The oxygen scavenger 10 is not particularly limited, and may include a reactor configured to react with oxygen gas found in air, a zinc/air cell, or another device that can provide reduced oxygen levels to the second volume 22, and thereby the first volume 14, when the cover layer 8 is sealed to the drape 6. The oxygen scavenger 10 is configured to react with oxygen gas in the second volume 22, by consuming oxygen in the second volume 22. A suitable oxygen scavenger is described in US 2014/0109890A1 or U.S. Pat. No. 8,012,169 B2. US 2014/0109890A1 describes an air activated heater that can be used to consume oxygen within the second volume 22, thus producing a reduced partial pressure of oxygen within the second volume 22. The oxygen scavenger 10 can include a reducing agent, a binding agent on a reactor substrate, and an electrolyte solution, which can be provided in an electrolyte impregnated pad. The reducing agent on the reactor substrate can be zinc, aluminum, or iron, for example. Other commercially available oxygen scavengers, e.g., iron fines, may also be employed.

Figures 3, 4:
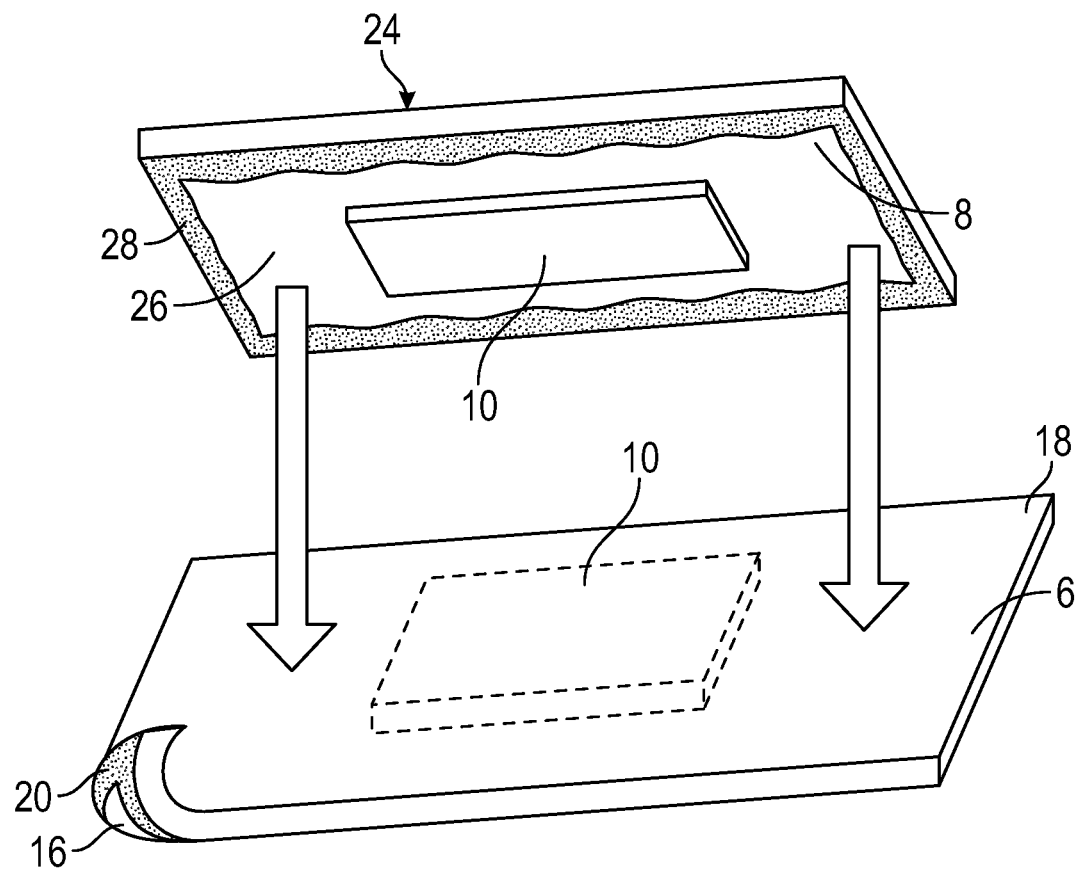
FIG. 3 is a schematic perspective view of a step of assembling a controlled oxygen dressing according to the present subject matter.
FIG. 4 is a schematic cross-sectional side view of a device including an oxygen scavenger and cover layer according to the present subject matter.

The oxygen scavenger 10 may be arranged on the bottom surface 26 of the cover layer 8 (FIGS. 2 and 3), or on the exposed surface 18 of the drape 6 (FIG. 3, shown in dotted lines). The oxygen scavenger 10 may be provided as part of a separate device 36 from the drape 6. Because of this, the cover layer 8 (with or without the oxygen scavenger 10) may be shipped, sold, and/or stored in a separate package from the drape 6 (with or without the oxygen scavenger 10).

The device 36 may include a release liner 38 that isolates the oxygen scavenger 10 from air/oxygen in a third volume 40, which may be air tight and free of oxygen. Before the cover layer 8 is sealed to the drape 6 (FIG. 3), and either before or after the drape 6 is adhered to the skin 12, the oxygen scavenger 10 may be activated by removing the release liner 38 from the device 36 by pulling on a tab portion 44 to thereby allow the oxygen scavenger 10 to be exposed to oxygen. When applied to the drape 6, the oxygen scavenger 10 consumes oxygen in the second volume 22, thus establishing across the covered portion 30 of the drape 6 an oxygen partial pressure differential between the first and second volumes 14, 22. Optionally, the oxygen scavenger 10 may be provided separately from the cover layer 8, and may be activated in a different manner. Alternatively, the dressing 2 may be provided in preassembled condition as shown in FIG. 2, where the cover layer 8 is already sealed to the drape 6 and the oxygen scavenger 10 is already arranged in the second volume 22. In this configuration, the dressing 2 may be applied to skin 12 around the tissue site 4 as a single component. In this configuration, the dressing 2 may be packaged in an oxygen-free environment in an air-tight container.

A controlled oxygen tissue treatment system 42 may include the drape 6, the oxygen scavenger 10, and a plurality of cover layers, for example cover layers 8A, 8B, 8C depicted in FIG. 1 and each corresponding to different areas $A_{R1}$, $A_{R2}$, $A_{R2}$, respectively, each of which may be smaller than the area ($A_D$) of the drape 6. These cover layers 8A, 8B, 8C and their respective areas may each correspond to a different predetermined oxygen level in the first volume 14. For example, sealing cover layer 8A onto the exposed surface 18 of the drape 6 may provide a level of about 15% oxygen in the first volume 14, cover layer 8B may provide about 10% oxygen in the first volume 14, and cover layer 8C may provide about 5% oxygen level in the first volume 14. These may provide other desired levels of oxygen in the first volume 14. Therefore, a user can choose, depending on the desired oxygen level in the first volume 14, which of the cover layers 8A, 8B, or 8C to seal to the drape 6. In the system 42, the oxygen scavenger 10 may be provided on the exposed surface 18 of the drape 6, may be provided separate from the drape 6 and separate from the cover layers 8A, 8B, 8C, or an oxygen scavenger 10 may be provided on the bottom surface 26 of each of the cover layers 8A, 8B, 8C. More or less than the three cover layers 8A, 8B, 8C of varying areas can be provided in the system 42.

A temperature-independent method of controlling oxygen around the tissue site 4 includes arranging the continuous drape 6 over the tissue site 4 to thereby define the first volume 14 between the drape 6 and the tissue site 4. The skin-facing surface 16 faces the tissue site 4 and the opposite exposed surface 18 faces away from the tissue site 4. The drape 6 is selectively permeable to air. The method includes determining, based on a desired oxygen level for the first volume 14, an area (covered portion 30) of the exposed surface 18 of the drape 6 that is to have restricted access/exposure to a surrounding environment 34 (i.e. surrounding atmosphere). The method includes covering the area (i.e. covered portion 30) with a cover layer 8 of equal area and having a permeability to air equal to or less than the drape 6, and thereby defining a covered portion 30 of the exposed surface 18 of the drape 6 and a second volume 22 between the cover layer 8 and the covered portion 30. The cover layer 8 restricts exposure of the covered portion 30 to the surrounding environment 34, and thus restricts ingress of air from the surrounding environment 34, through the covered portion 30, and into the first volume 14. The method includes arranging the oxygen scavenger 10 in the second volume 22 to thereby remove oxygen from the second volume 22, which produces an oxygen level in the first volume 14 lower than in the surrounding environment 34.

The oxygen level in the first volume 14 is a function of a ratio of the area ($A_R$) of the cover layer 8/covered portion 30 relative to an area ($A_D$) of the drape 6. The oxygen scavenger 10 may be arranged in the second volume 22 before sealing the cover layer 8 to the exposed surface 18.

A method of manufacturing the dressing system 42 includes preparing the continuous drape 6, which is selectively permeable to air, has a first area ($A_D$), includes the skin-facing surface 16, the opposite exposed surface 18, and an adhesive gasket 20 on the skin-facing surface 16 configured to adhere the drape 6 to skin 12 and thereby define the first volume 14 between the skin-facing surface 16 and the skin 12. The method includes preparing the cover layer 8, which has permeability to air equal to or less than the drape

6, and includes a bottom surface 26, and a seal 28 on the bottom surface 26 configured to seal the cover layer 8 to the exposed surface 18 and thereby cover a covered portion 30 of the exposed surface 18 and define a second volume 22 between the cover layer 8 and the covered portion 30. The method includes arranging an oxygen scavenger 10 on the exposed surface 18 of the drape 6 or on the bottom surface 26 of the cover layer 8 such that when the cover layer 8 is sealed to the exposed surface 18, the oxygen scavenger 10 is arranged in the second volume 22 to thereby remove oxygen from the second volume 22 and provide a desired level of oxygen in the first volume 14.

The method may further include sterilizing the drape 6, optionally anything that may come into contact with the skin 12 such an absorbent layer or skin contacting layer, and optionally the removable release liner 38, and then sealing the cover layer 8 to the exposed surface 18 such that the cover layer 8 restricts ingress of air from the surrounding environment 34, through the covered portion 30, and into the first volume 14, and only allows air from the surrounding environment 34 to be transmitted through the non-covered portion 32 of the drape 6. Because the drape 6 is continuous, and because the tissue site 4 is only exposed to the drape 6, only the drape 6 has to be sterilized. The cover layer 8 and oxygen scavenger do not have to be sterilized because the tissue site 4 is not exposed to these two components. As such, the cover layer 8 and the oxygen scavenger 10 may or may not be sterilized. Alternatively, all of the drape 6, cover layer 8, and oxygen scavenger 10 may be sterilized.

The method may further include packaging each of the drape 6 and the cover layer 8 in a configuration where the cover layer 8 is not sealed to the exposed surface 18 of the drape 6. This may be accomplished by packaging the device 36 in a package for storage, transport, or sale, that is separate from a package containing the drape 6. A user may then open the separate packages, and first adhere the drape 6 to skin 12, and then separately seal the cover layer 8 to the drape 6 (FIG. 3). Alternately, the dressing 2 may be preassembled as in FIG. 2 and applied to skin 12 around the tissue site 4 as a single component.

It will be appreciated that various of the above-disclosed embodiments and other features and functions, or alternatives or varieties thereof, may be desirably combined into many other different systems or applications. Also that various presently unforeseen or unanticipated alternatives, modifications, variations or improvements therein may be subsequently made by those skilled in the art which are also intended to be encompassed by the following claims.

The invention claimed is:

1. A controlled oxygen dressing for tissue treatment, the dressing comprising:
  a flexible drape being permeable to air, having a first area, including a skin-facing surface and an exposed surface which is opposite the skin-facing surface, the drape being made from a thin flexible continuous sheet that does not include openings extending from the skin-facing surface to the exposed surface that allow bulk transfer or a continuum flow of air through the openings, and being configured to be adhered to skin and thereby define a first volume around a tissue site between the skin-facing surface and the skin;
  an adhesive gasket arranged around a periphery of the skin-facing surface of the drape to adhere the dressing to the skin;
  a cover layer configured to be sealed to the exposed surface and thereby cover a covered portion of the exposed surface of the drape and define a second volume between the cover layer and the covered portion; and
  an oxygen scavenger configured to be arranged in the second volume to remove oxygen from the second volume such that oxygen from the first volume permeates through the covered portion of the drape to provide a desired level of oxygen in the first volume,
  wherein the cover layer has a second area smaller than the first area of the drape configured to provide the desired level of oxygen for the first volume, and
  wherein when the cover layer is sealed to the drape, a non-covered portion of the drape is provided between a periphery of the cover layer and the adhesive gasket, wherein oxygen from a surrounding environment is limited to diffusing into the first volume through the non-covered portion of the drape and a pressure within the first volume around the tissue site is maintained at about atmospheric pressure and not lowered to between −60 and −125 mmHg with respect to atmospheric pressure.

2. The dressing according to claim 1, wherein the cover layer has an oxygen transmission rate through its thickness normalized to 1 mil, at standard temperature and pressure and 0% relative humidity, of less than 30 $cm^3/m^2/24$ hr.

3. The dressing according to claim 2, wherein the cover layer comprises a polymer film coated with metal, polyvinylidene chloride, polyvinyl alcohol, or combinations thereof.

4. The dressing according to claim 3, wherein the cover layer comprises a metalized polymer film.

5. The dressing according to claim 1, wherein:
  the cover layer has a permeability to air less than the drape,
  the oxygen scavenger is arranged in the second volume; and
  removal of oxygen from the second volume causes oxygen to be removed from the first volume, be transmitted through the covered portion, and enter into the second volume to be scavenged by the oxygen scavenger.

6. The dressing according to claim 1, further comprising a seal arranged around a periphery of the cover layer to seal the cover layer to the exposed surface of the drape,
  wherein the oxygen scavenger is arranged within a perimeter formed by the seal.

7. A temperature-independent method of controlling oxygen around a tissue site using an oxygen tissue treatment system, the method comprising:
  arranging a flexible drape over the tissue site to thereby define a first volume between the drape and the tissue site, the drape including a skin-facing surface facing the tissue site and an exposed surface facing away from the tissue site, and the drape being permeable to air;
  determining, by a user of the oxygen tissue treatment system, a portion of the exposed surface of the drape that is to have restricted exposure to a surrounding atmosphere based on a desired oxygen level for the first volume;
  selecting, by a user of the oxygen tissue treatment system, a cover layer among a plurality of provided cover layers each having different respective areas, wherein each cover layer among the provided cover layers corresponds to a different predetermined oxygen level in the first volume;
  covering the portion with at least one cover layer among the plurality of provided cover layers, thereby defining a covered portion of the exposed surface of the drape and a second volume between the at least one cover layer and the covered portion, the at least one cover layer restricting ingress of air from the surrounding atmosphere, through the covered portion, and into the first volume; and arranging an oxygen scavenger in the second volume to thereby remove oxygen from the second volume, which produces an oxygen level in the first volume lower than in the surrounding atmosphere.

8. The method according to claim 7, wherein:

each cover layer has a permeability to air less than the drape, and the oxygen level in the first volume is a function of a ratio of an area of the covered portion relative to an area of the drape.

9. The method according to claim 8, wherein the area of the covered portion is smaller than the area of the drape.

10. The method according to claim 7, wherein the oxygen scavenger is arranged in the second volume before sealing the cover layer to the exposed surface.

11. The method according to claim 10, wherein the oxygen scavenger is activated after the drape is adhered to the skin.

12. The method according to claim 7, wherein the drape is adhered to the skin by an adhesive gasket arranged around a periphery of the skin-facing surface of the drape.

13. The method according to claim 7, wherein:

the at least one cover layer is sealed to the exposed surface by a seal arranged around a periphery of the cover layer; and the oxygen scavenger is arranged within a perimeter formed by the seal.

14. The method according to claim 7, wherein each cover layer includes a metalized polymer film and has an oxygen transmission rate through its thickness normalized to 1 mil, at standard temperature and pressure and 0% relative humidity, of less than 30 $cm^3/m^2/24$ hr.

* * * * *